(12) United States Patent
Kunardi

(10) Patent No.: US 12,201,791 B2
(45) Date of Patent: Jan. 21, 2025

(54) INTRAVENOUS DEVICE ASSEMBLY WITH NEEDLE GUARD

(71) Applicant: Becton, Dickinson and Company, Franklin Lakes, NJ (US)

(72) Inventor: Linda Kunardi, Singapore (SG)

(73) Assignee: Becton, Dickinson and Company, Franklin Lakes, NJ (US)

( * ) Notice: Subject to any disclaimer, the term of this patent is extended or adjusted under 35 U.S.C. 154(b) by 164 days.

(21) Appl. No.: 17/208,941

(22) Filed: Mar. 22, 2021

(65) Prior Publication Data

US 2021/0299409 A1 Sep. 30, 2021

Related U.S. Application Data

(60) Provisional application No. 63/003,004, filed on Mar. 31, 2020.

(51) Int. Cl.
*A61M 25/06* (2006.01)
*A61M 5/162* (2006.01)
(Continued)

(52) U.S. Cl.
CPC .... *A61M 25/0618* (2013.01); *A61M 25/0606* (2013.01); *A61M 25/0625* (2013.01);
(Continued)

(58) Field of Classification Search
CPC .......... A61M 25/0618; A61M 25/0631; A61M 25/0625; A61M 25/0606; A61M 39/10;
(Continued)

(56) References Cited

U.S. PATENT DOCUMENTS

2008/0306450 A1* 12/2008 Martin .................. A61M 5/326
604/195
2009/0281499 A1* 11/2009 Harding ............ A61M 25/0618
604/164.08

(Continued)

FOREIGN PATENT DOCUMENTS

AU 2014287348 A1 2/2016
AU 2016344419 A1 4/2018
(Continued)

*Primary Examiner* — William R Carpenter
*Assistant Examiner* — Robert F Allen
(74) *Attorney, Agent, or Firm* — Kirton McConkie; Whitney Blair; Kevin Stinger

(57) ABSTRACT

An intravenous (IV) device assembly may include a catheter adapter and a needle guard residing within a bore of the catheter adapter. The needle guard may include a needle formed through a guard bore. The guard bore may include a first internal diameter along a first bore portion and a second internal diameter, smaller than the first bore portion, along a second bore portion. A clip may be coupled to the exterior surface of the needle guard. The clip may include a first arm, which may include a first end guard, and a second arm, which may include a second end guard. The clip may be slidable distally along the exterior surface of the needle guard to move from an open configuration to a closed configuration, thereby blocking distal motion of the needle within the needle guard.

6 Claims, 9 Drawing Sheets

(51) Int. Cl.
*A61M 5/32* (2006.01)
*A61M 25/00* (2006.01)
*A61M 39/10* (2006.01)

(52) U.S. Cl.
CPC ........... *A61M 39/10* (2013.01); *A61M 5/1626* (2013.01); *A61M 2005/3247* (2013.01); *A61M 2005/325* (2013.01); *A61M 5/3273* (2013.01); *A61M 5/329* (2013.01); *A61M 25/0097* (2013.01); *A61M 25/0631* (2013.01); *A61M 2039/1072* (2013.01); *A61M 2039/1077* (2013.01)

(58) Field of Classification Search
CPC ...... A61M 2039/1077; A61M 25/0097; A61M 5/158; A61M 2039/1072; A61M 5/329; A61M 5/3273; A61M 5/1626; A61M 2005/3247; A61M 2005/325
See application file for complete search history.

(56) References Cited

U.S. PATENT DOCUMENTS

| | | | |
|---|---|---|---|
| 2010/0222746 A1* | 9/2010 | Burkholz | A61M 25/0606 604/164.08 |
| 2012/0046620 A1* | 2/2012 | Woehr | A61M 25/0097 604/263 |
| 2012/0220957 A1* | 8/2012 | Kuracina | A61M 25/0097 604/263 |
| 2013/0023835 A1* | 1/2013 | Kuracina | A61M 5/1626 604/263 |
| 2013/0138015 A1 | 5/2013 | Kuracina | |
| 2013/0204207 A1 | 8/2013 | Kuracina | |
| 2014/0012210 A1 | 1/2014 | Kuracina et al. | |
| 2015/0126943 A1 | 5/2015 | Kuracina et al. | |
| 2015/0352332 A1 | 12/2015 | Kuracina et al. | |
| 2017/0120010 A1* | 5/2017 | Burkholz | A61M 5/1626 |
| 2018/0043093 A1 | 2/2018 | Nakagami et al. | |
| 2018/0050151 A1 | 2/2018 | Kuracina | |
| 2018/0214682 A1* | 8/2018 | Woehr | A61M 39/0247 |
| 2018/0289932 A1* | 10/2018 | Isaacson | A61M 25/0693 |
| 2019/0001074 A1* | 1/2019 | Knutsson | A61M 5/3245 |
| 2019/0030292 A1* | 1/2019 | Isaacson | A61M 5/3273 |
| 2019/0160264 A1* | 5/2019 | Isaacson | A61M 39/0693 |
| 2019/0374710 A1 | 12/2019 | Kuracina | |
| 2020/0155808 A1 | 5/2020 | Burkholz et al. | |
| 2022/0280756 A1* | 9/2022 | Woehr | A61M 5/3271 |

FOREIGN PATENT DOCUMENTS

| | | |
|---|---|---|
| CA | 2920351 A1 | 1/2015 |
| CA | 3001701 A1 | 5/2017 |
| CN | 105377353 A | 3/2016 |
| CN | 106620995 A | 5/2017 |
| CN | 206652049 U | 11/2017 |
| CN | 113117216 A | 7/2021 |
| EP | 3019229 A1 | 5/2016 |
| EP | 3238770 | 11/2017 |
| EP | 3368127 A1 | 9/2018 |
| EP | 3736011 A1 | 11/2020 |
| EP | 3744382 A1 | 12/2020 |
| ES | 2821327 T3 | 4/2021 |
| ES | 2831758 T3 | 6/2021 |
| JP | 2016526469 A | 9/2016 |
| JP | WO2016080525 A1 | 9/2017 |
| JP | 2018536471 A | 12/2018 |
| JP | 6731154 B2 | 7/2020 |
| JP | 2020146533 A | 9/2020 |
| SG | 11201802861V A | 5/2018 |
| WO | 2015/006340 | 1/2015 |
| WO | 2017074684 A1 | 5/2017 |

* cited by examiner

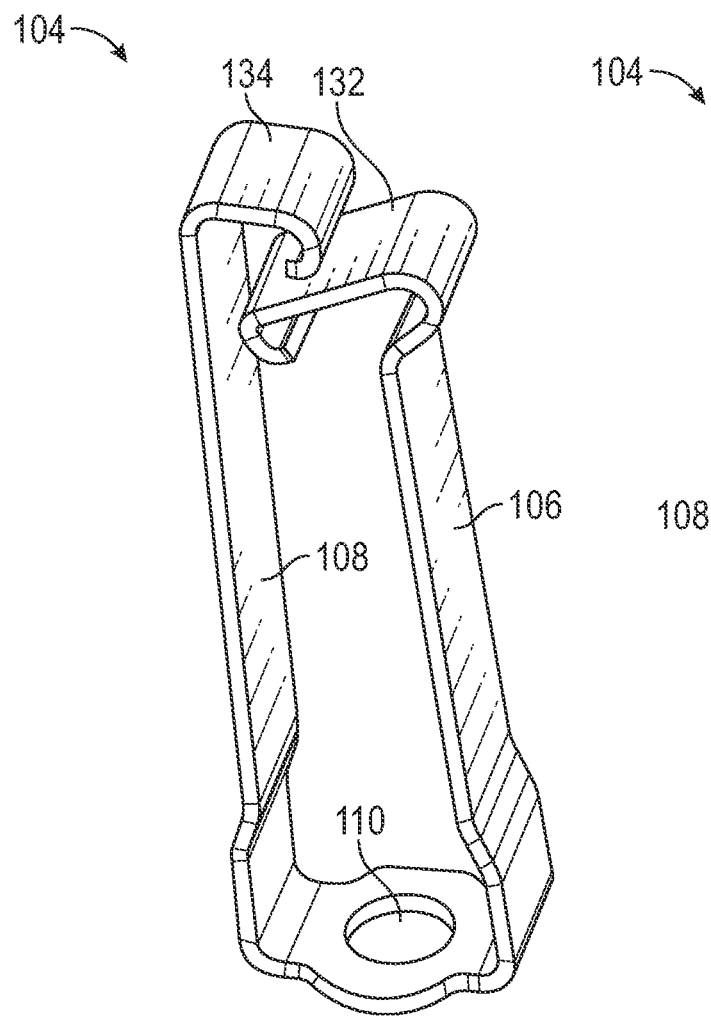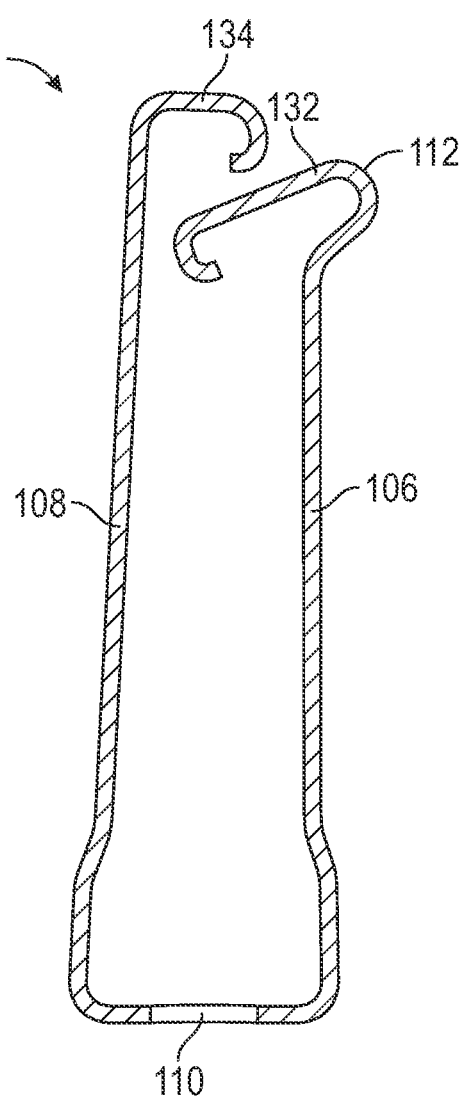
FIG. 4A
FIG. 4B

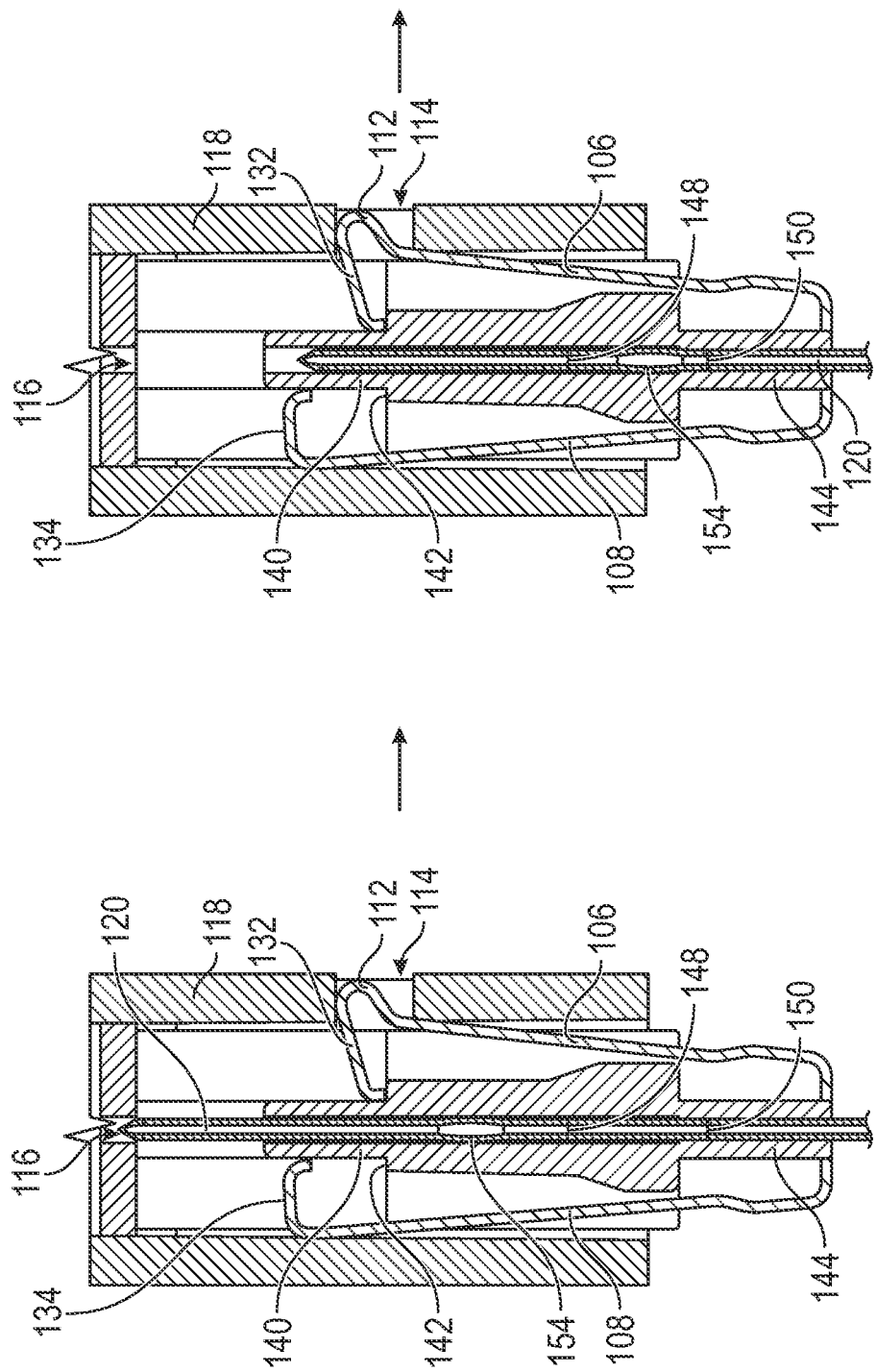

INTRAVENOUS DEVICE ASSEMBLY WITH NEEDLE GUARD

RELATED APPLICATIONS

This application claims the benefit of U.S. Provisional Patent Application No. 63/003,004, filed on Mar. 31, 2020, entitled INTRAVENOUS DEVICE ASSEMBLY WITH NEEDLE GUARD, which is incorporated herein in its entirety.

BACKGROUND

Intravenous (IV) device assemblies are among the various types of vascular access devices (VADs). IV catheter configuration may include over-the-needle IV catheters. As its name implies, an over-the-needle IV catheter may be mounted over an introducer needle having a sharp distal tip. The needle may be a hypodermic needle coupled to a needle assembly to help guide the needle and to facilitate its cooperation with the catheter. At least the inner surface of the distal portion of the catheter may engage an outer surface of the needle to prevent peel back of the catheter and, thereby, facilitate insertion of the catheter into the blood vessel. The catheter and the needle may be assembled so that the distal tip of the needle extends beyond the distal tip of the catheter. Moreover, the catheter and the needle may be assembled so that, during insertion, the bevel of the needle faces up, away from skin of a patient. The catheter and needle may be inserted at a shallow angle through the skin into a blood vessel.

In order to verify proper placement of the needle and/or catheter in the blood vessel, the user may confirm that there is "flashback" of blood into a flashback chamber associated with the needle assembly. Flashback generally entails the appearance of an amount of blood, which is visible within the needle assembly or between the needle and the catheter. In response to proper placement of the distal tip of the catheter into the blood vessel being confirmed, the user may apply pressure to the blood vessel by pressing down on the skin over the blood vessel, distal to the needle and the catheter. This finger pressure may momentarily occlude the vessel, reducing further blood flow through the needle and the catheter.

A clinician or other health care provider (HCP) may then withdraw the needle from the catheter, and in some instances, the needle assembly may be separated from catheter portions of the catheter assembly. The separation of the needle assembly from catheter portions of the catheter assembly presents numerous potential hazards to the users and others in the area. There may be a risk of accidental needle sticks if the distal tip is not secured properly. Additionally, because the needle has been in contact with blood in vasculature of the patient, blood may be present on an exterior of the needle as well as inside a lumen of the needle. As the needle is withdrawn from the catheter, there is a risk that the blood will drip from the distal tip or come into contact with other surfaces to expose people and equipment to blood.

Additionally, withdrawing the needle from a catheter assembly may impart energy to parts of the needle assembly. For instance, during withdrawal of the introducer, bending forces can be applied (either unintentionally or intentionally) to the needle. The bending forces on the needle may cause blood to splatter or spray from the needle when the needle vibrates and shakes as it becomes free from the catheter assembly and releases stored energy.

The subject matter claimed herein is not limited to embodiments that solve any disadvantages or that operate only in environments such as those described herein. Rather, this background is provided to describe an environment in which the presently described embodiments may operate.

SUMMARY

The present disclosure relates generally to an intravenous (IV) device assembly that provides for a fluidic path through the IV device assembly while reducing a likelihood of any accidental needle sticks, spreading of blood outside of the fluidic path, and spraying of blood during withdrawal of the needle from the IV device assembly. In some embodiments, the IV device assembly may include a catheter adapter, which may include a distal end, a proximal end, and an adapter bore formed axially therein. In some embodiments, a needle guard may be disposed within the bore of the catheter adapter. In some embodiments, the needle guard may include a guard bore formed through the needle guard to receive a needle therethrough. In some embodiments, the guard bore may include a first internal diameter along a first bore portion of the guard bore and a second internal diameter, smaller than the first bore portion, along a second bore portion of the guard bore. In some embodiments, the second internal diameter may be sufficiently small to urge the needle to remain within the needle guard.

In some embodiments, the needle guard may include an exterior surface onto which a clip is coupled. In some embodiments, the clip may include a clip retention feature that cooperates with a catheter adapter retention feature of the catheter adapter to urge the needle guard to remain in place within the adapter bore. In some embodiments, the clip may include a first arm, which may include a first end guard, and a second arm, which may include a second end guard. In some embodiments, the clip may be slidable distally along the exterior surface of the needle guard. In some embodiments, in response to withdrawal of the needle guard from the adapter bore, the clip may move from an open configuration, in which the needle is movable distally within the needle guard, to a closed configuration, in which at least one of the first end guard and the second end guard is positioned to block distal motion of the needle within the needle guard.

In some embodiments, the IV device assembly may include a hole formed in the clip through which a stem of the needle guard is selectively passed as the needle guard and the clip pass through the catheter adapter. In some embodiments, the IV device assembly may include a stepped shoulder portion formed within the needle guard wherein the stepped shoulder portion prevents the first end guard and the second end guard from contacting the needle. In some embodiments, the IV device assembly may include a septum placed between the needle guard and a distal end of the catheter adapter for the needle to pierce and exit the distal end of the IV device assembly. In some embodiments, the IV device may include a bump formed on the needle to interface with the guard bore at the second internal diameter and drag the needle guard to a proximal end of the IV device assembly and sheath a bevel end of the needle within the needle guard in response to the withdrawal of the needle guard from the adapter bore.

In some embodiments, the IV device assembly may include a proximal port formed through a distal end of the needle guard to allow the needle to pass therethrough. In some embodiments, the IV device assembly may include multiple rails formed on the needle guard to interface with an interior surface of the catheter adapter to restrict rotation of the needle guard from the adapter bore in response to the withdrawal of the needle guard from the adapter bore. In some embodiments, the IV device assembly may include a stepped channel formed within the needle guard to allow the first arm and the second arm to be deformed into the needle guard. In some embodiments, the IV device assembly may include a center opening into which the first end guard and the second end guard are biased into in response to the withdrawal of the needle guard from the adapter bore placing the clip is in the closed configuration.

The present disclosure further describes, in some embodiments, an IV device assembly that includes a catheter adapter that includes a distal end, a proximal end, and an adapter bore formed axially therein. In these and other embodiments, a needle guard may reside within the adapter bore of the catheter adapter. In some embodiments, the needle guard may include a guard bore formed through the needle guard to receive a needle therethrough. In some embodiments, the guard bore may include a first internal diameter along a first bore portion of the guard bore, and a second internal diameter, smaller than the first bore portion, along a second bore portion of the guard bore. In some embodiments, the needle guard may include an exterior surface. In these and other embodiments, a needle may include a catch shaped to abut against the second internal diameter. In some embodiments, a clip may be coupled to the exterior surface of the needle guard. In some embodiments, the clip may include a clip retention feature that cooperates with a catheter adapter retention feature of the catheter adapter to urge the needle guard to remain in place within the adapter bore. In some embodiments, the clip may include a first arm, which may include a first end guard, and a second arm, which may include a second end guard.

In some embodiments, the second internal diameter may be sufficiently small to urge the needle to remain within the needle guard when the catch engages the second internal diameter. In some embodiments, in response to withdrawal of the needle guard from the adapter bore, the clip may be slidable distally along the exterior surface to move from an open configuration, in which the needle is movable distally within the needle guard, to a closed configuration, in which at least one of the first end guard and the second end guard is positioned to block distal motion of the needle within the needle guard. In some embodiments, the IV device assembly may include a septum placed between the needle guard and a distal end of the catheter adapter for the needle to pierce and exit the distal end of the IV device assembly. In some embodiments, the catch may be a bump on the needle to interface with the guard bore at the second internal diameter. In some embodiments, the catch may be a detent on the needle to interface with a bump on the guard bore at the second internal diameter. In some embodiments, the catch may include both the bump and detent, which may cooperate to abut against and interface with corresponding structures within the guard bore at the second internal diameter.

In some embodiments, the present disclosure further describes a vascular access device (VAD) that includes a catheter adapter, which may include a distal end, a proximal end, and an adapter bore formed axially therein and a needle guard residing within the adapter bore of the catheter adapter. In some embodiments, the needle guard may include a guard bore formed through the needle guard to receive a needle therethrough. In some embodiments, the guard bore may include a first internal diameter along a first bore portion of the guard bore, and a second internal diameter, smaller than the first bore portion, along a second bore portion of the guard bore.

In some embodiments, the VAD may further include a clip coupled to an exterior surface of the needle guard. In some embodiments, the clip may include a first arm, which may include a first end guard, a second arm, which may include a second end guard. In these and other embodiments, the second internal diameter may be sufficiently small to urge the needle to remain within the needle guard. Additionally, in this embodiment, the clip and needle guard may be slidable within the adapter bore, and in response to withdrawal of the needle guard from the adapter bore the clip may be moved from an open configuration, in which the needle and the needle guard is movable distally within the needle guard, to a closed configuration. In some embodiments, in the closed configuration, at least one of the first end guard and the second end guard is positioned within a center opening formed in the needle guard and across the guard bore to block distal motion of the needle within the needle guard. In some embodiments, the VAD may include a hole formed in the clip through which a stem of the needle guard is selectively passed as the needle guard and the clip pass through the catheter adapter.

In some embodiments, the VAD may include a septum placed between the needle guard and a distal end of the catheter adapter for the needle to pierce and exit the distal end of the VAD. In some embodiments, the VAD may include a bump formed on the needle to abut with the guard bore at the second internal diameter to the withdrawal of the needle guard from the adapter bore. In some embodiments, the VAD may include a stepped channel formed into the needle guard to allow the first arm and the second arm to be deformed into a body of the needle guard; and a stepped shoulder portion formed into the needle guard to prevent the clip from contacting the needle. In some embodiments, the VAD may include a detent formed on the needle to interface with a bump on the guard bore at the second internal diameter.

It is to be understood that both the foregoing general description and the following detailed description are examples and explanatory and are not restrictive of the invention, as claimed. It should be understood that the various embodiments are not limited to the arrangements and instrumentality illustrated in the drawings. It also be understood that the embodiments may be combined, or that other embodiments may be utilized and that structural changes, unless so claimed, may be made without departing from the scope of the various embodiments of the present invention. The following detailed description is, therefore, not to be taken in a limiting sense.

BRIEF DESCRIPTION OF THE SEVERAL VIEWS OF THE DRAWINGS

Example embodiments will be described and explained with additional specificity and detail through the use of the accompanying drawings in which:

FIG. 4A is a perspective view of clip according to an embodiment of the present disclosure;

FIG. 4B is a side elevation view of a clip according to an embodiment of the present disclosure;

FIG. 6A is a side elevation, section view of an IV device assembly according to an embodiment of the present disclosure;

FIG. 6B is a side elevation, section view of an IV device assembly according to an embodiment of the present disclosure;

DESCRIPTION OF EMBODIMENTS

As used herein, the term "proximal" refers to a location on the element being described that, during use, is closest to the clinician using the device and farthest from the patient in connection with whom the device is used. The term "distal" refers to a location on the element being described that, during use, is farthest from the clinician using the device and closest to the patient in connection with whom the device is used.

As used herein, the term "top", "up" or "upwardly" refers to a location on the needle of this intravenous therapy system that, during use, is radially away from the longitudinal axis of the intravenous therapy system and away from the patient's skin. As used herein, the term "bottom", "down" or "downwardly" refers to a location on the needle of this intravenous therapy system that, during use, is radially away from the longitudinal axis of the device and toward the patient's skin.

As used herein, the term "in" or "inwardly" refers to a location with respect to the needle of this intravenous therapy system that, during use, is toward the inside of the intravenous therapy system. As used herein, the term "out" or "outwardly" refers to a location with respect to the needle of this intravenous therapy system that, during use, is toward the outside of the intravenous therapy system.

Although the embodiments described herein are used in connection for use as an IV device assembly to receive a blood sample or introduce a medicament into the body of a patient, it is to be understood that the use of the IV device assembly is applicable to other medical devices as well.

Figure 1:
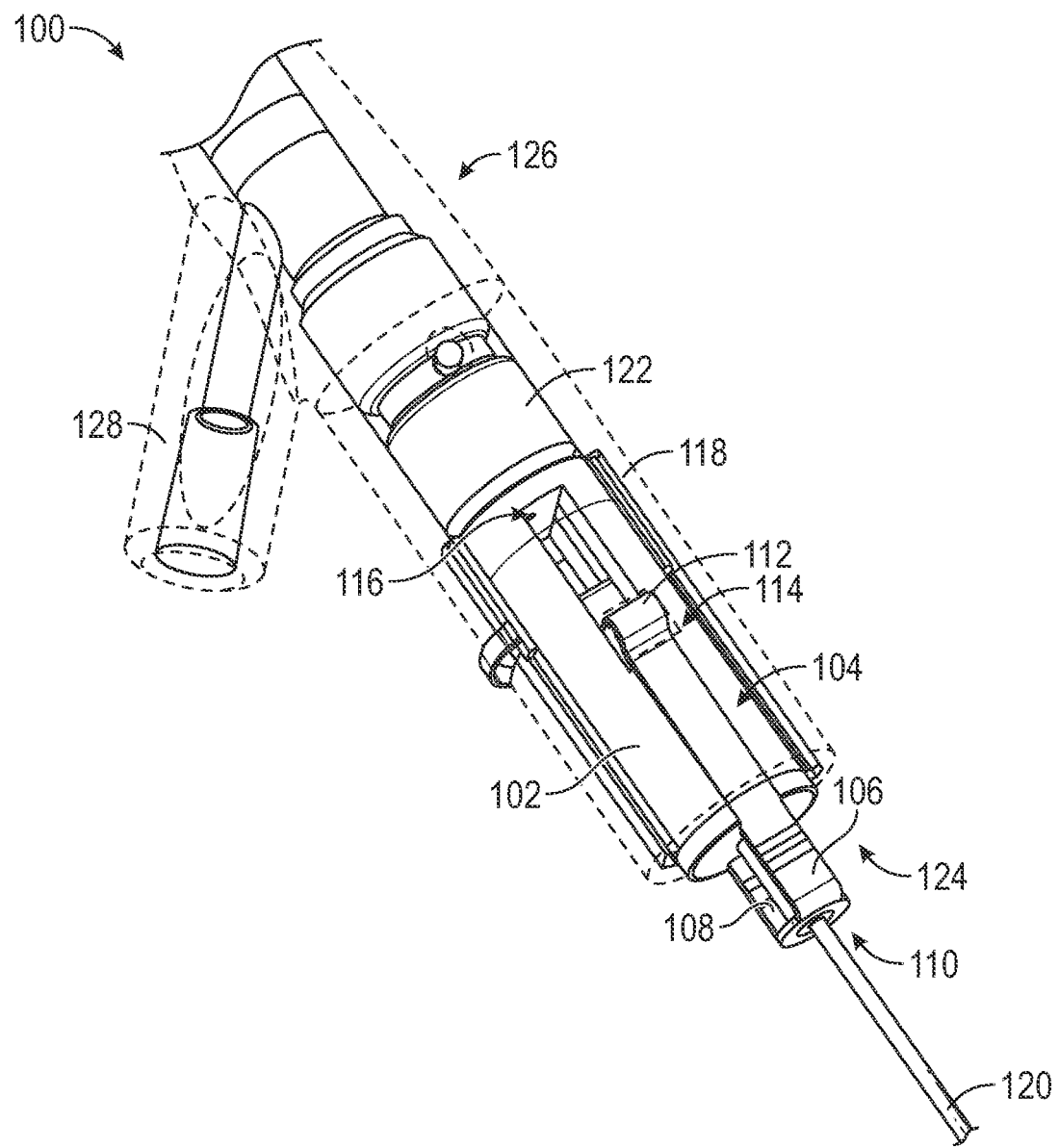
FIG. 1 is a perspective view of an intravenous (IV) device assembly according to an embodiment of the present disclosure.

FIG. 1 is a perspective view of an intravenous (IV) device assembly 100 according to some embodiments of the present disclosure. In some embodiments, the IV device assembly 100 may include a distal end 126 and a proximal end 124. In some embodiments, at the distal end 126, the IV device assembly 100 may be mechanically and fluidically coupled to an IV catheter (not illustrated in FIG. 1). In some embodiments, at the proximal end 124, the IV device assembly 100 may be mechanically and fluidically coupled to, for example, a blood drawing apparatus such as a BD VACUTAINER® LUER-LOK™ Access Device produced by Becton, Dickinson and Company of Franklin Lakes, N.J., United States of America. In some embodiments, these devices may form, therethrough, a fluidic path for transfer of blood from a patient's body or the introduction of an infusing fluid, such as saline solution, various medicaments, and/or total parenteral nutrition, into a patient.

In some embodiments, the IV device assembly 100 may include a catheter adapter 118 that may be placed intermediary to the proximal end 124 and the distal end 126 of the IV device assembly 100. In some embodiments, the catheter adapter 118 may include an adapter bore formed along a long axis of the catheter adapter 118. In some embodiments, the adapter bore may be formed to fit a septum 122 and a needle guard 102 therein. In some embodiments, the septum 122 may be pierced by a needle 120 that is placed within the IV device assembly 100. In some embodiments, the septum 122 may be made of a silicone or rubber that allows for the needle 120 to pierce through the septum 122 and create a fluidic seal when the needle 120 is pulled out of the septum 122.

In some embodiments, the needle guard 102 may also be placed within the adapter bore. In some embodiments, the needle guard 102 may be made of a plastic, a metal, or other type of resilient material that may slide within the adapter bore in response to a withdrawal of the needle guard from the adapter bore as described herein. In some embodiments, the needle guard 102 may be made of a material that produces the least amount of friction between the exterior surface of the needle guard 102 and an interior surface of the bore formed through the catheter adapter 118 so that the needle guard 102 may be pulled through the adapter bore upon application of a force by the clinician or other HCP.

In some embodiments, the needle guard 102 may include a guard bore 116 through which a needle 120 may be passed. In some embodiments, the needle 120 may be placed in a deployed state such that the needle 120 extends out of the catheter adapter 118 and into an IV catheter. In some embodiments, the length of the needle 120 may be such that the needle 120 extends past a terminal end of a catheter of the IV catheter mechanically and fluidically coupled to the catheter adapter 118. In some embodiments, in this deployed state, the needle 120 may pass through the guard bore 116 and the septum 122 and through the length of the catheter adapter 118. In some embodiments, the clinician or other HCP may be provided with the IV device assembly 100 that has a needle 120 in this deployed state.

In some embodiments, as described herein, the needle guard 102 may include a clip 104. The clip 104 may be made of an elastically resilient material such as a metal. In the present disclosure and in the appended claims, the term "elastically resilient" may be defined as the ability of a material to return to a neutral state after being subject to a tensioning force.

In some embodiments, the clip 104 may include a first arm 106 and a second arm 108. In some embodiments, the first arm 106 and the second arm 108 may be passed along an exterior surface of the needle guard 102. In some embodiments, distal ends of the first arm 106 and the second arm 108 may be elastically biased toward a longitudinal axis of the needle guard 102 such that a force is applied to an exterior surface of the needle guard 102.

In some embodiments, in order to accommodate the mechanical coupling of the clip 104 to the needle guard 102, the needle guard 102 may include a stepped channel formed into the needle guard 102 for interfacing with the clip 104 and preventing the axial rotation of the clip 104 relative to the longitudinal axis of the needle guard 102. In some embodiments, the stepped channel may be stepped such that a proximal end of the needle guard 102 at the stepped channel is wider than at an intermediate location along the length of the needle guard 102. In some embodiments, the stepped channel may end at a location along the longitudinal axis of the needle guard 102 that is intermediate to the distal end and the proximal end of the needle guard 102. In some embodiments, the stepped channel may terminate at a stepped shoulder portion that a first end guard of the first arm 106 and a second end guard of the second arm 108 rests on as the needle 120 is in its deployed state.

In some embodiments, the clip 104 may include a clip retention feature 112. In some embodiments, the clip retention feature 112 may be a bent portion of the first arm 106 close to a first end guard formed at a distal end of the first arm 106. In some embodiments, the clip retention feature 112 may interface with the catheter adapter 118 so that the clip 104 may be maintained in position relative to the catheter adapter 118 when the needle 120 is in its deployed state. In some embodiments, the clip retention feature 112 may interface with a window 114 formed through a wall of the catheter adapter 118. In some embodiments, the clip retention feature 112 may maintain the clip 104 at a specific location along the adapter bore until the needle 120 is moved proximally through the catheter adapter 118. In some embodiments, when the needle 120 is moved proximally through the catheter adapter 118, the clip may be pulled or may slide within the catheter adapter 118.

In some embodiments, a portion of the clip 104 where the proximal ends of the first arm 106 and second arm 108 meet may include a hole 110 formed therethrough. In some embodiments, the hole 110 may be used to pass a stem of the needle guard 102 therethrough. In some embodiments, the stem interfacing with the hole 110 may prevent the clip 104 from moving orthogonally away from a longitudinal axis formed by the guard bore 116. Additionally, in some embodiments, the needle 120 may pass through the stem and the hole 110 so that the needle 120 may be pulled proximally through the needle guard 102 as described herein.

As described, in some embodiments, the IV device assembly 100 may include a needle 120 that passes through a guard bore 116 formed through the needle guard 102. In some embodiments, the guard bore 116 may include a first internal diameter along a first bore portion of the guard bore 116 and a second internal diameter along a second bore portion of the guard bore 116 and smaller than the first bore portion. In some embodiments, the second bore portion may be proximal to the first bore portion along the longitudinal axis of the needle guard 102.

In some embodiments, the needle 120 may also include a catch to interface with the second bore portion as the needle 120 is slid proximally through the needle guard 102. In some embodiments, the catch may be a bump formed on the needle. In these and other embodiments, a diameter of the bump on the needle may be larger than the second internal diameter such that, as the needle is retracted proximally through the guard bore 116, the bump urges the needle 120 to remain within the needle guard 102. This may be done by the bump abutting with the smaller diameter guard bore 116 having the second internal diameter. This may cause the needle guard 102 to be pulled towards the proximal end of the catheter adapter 118. In some embodiments, the catch of the needle 120 may be in the form of a detent formed on the needle 120. In these and other embodiments, the guard bore 116 may include a bump formed on the interior surface of the second bore portion to interface with the detent such that, as the needle 120 is retracted proximally through the guard bore 116, the detent and bump urges the needle to remain within the needle guard 102. This may cause the needle guard 102 to be pulled towards the proximal end of the catheter adapter 118.

In some embodiments, the needle guard 102 may further include a center opening which the first end guard of the first arm 106 and the second end guard of the second arm 108 are biased into in response to the withdrawal of the needle guard through the adapter bore and from the IV catheter and septum 122. In some embodiments, the center opening may be an opening formed through the needle guard 102 such that the center opening passes through the needle guard 102 perpendicular to the longitudinal axis of the needle guard 102. In some embodiments, the center opening may be placed at a location along the longitudinal axis of the needle guard 102 such that a retraction of the needle 120 into the needle guard 102 causes the needle 120 to be moved proximally past the center opening.

In some embodiments, the IV device assembly 100 may include an assembly port 128. In some embodiments, the assembly port 128 may include a bore formed therethrough in order to form a fluidic channel with the catheter mechanically and fluidically coupled to the catheter adapter 118. In some embodiments, the assembly port 128 may be used for introducing an infusing fluid, such as saline solution, various medicaments, and/or total parenteral nutrition, into a patient.

The action of the IV device assembly 100 will now be described, according to some embodiments. As described herein, in some embodiments, the clinician or other HCP may receive the IV device assembly 100 in a state where the needle 120 is deployed and extending through the septum 122, out of the catheter adapter 118, and past a terminal end of a catheter (not illustrated) of an IV catheter mechanically and fluidically coupled to the catheter adapter 118. In some embodiments, the IV catheter may be inserted into a patient's body with the aid of a bevel edge of the needle 120. In some embodiments, in response to the IV catheter being in place, the needle may be drawn, proximally, out of the catheter and through the septum 122 and needle guard 102. In some embodiments, in addition to the needle 120 being extended out of the catheter adapter 118 and past a terminal end of the catheter of the IV catheter, the clip retention feature 112 may be fixed within the window 114 thereby retaining the clip 104 at a location within the catheter adapter 118 in what may be referred herein as an open configuration. In some embodiments, the open configuration is descriptive of a configuration of the clip 104 such that the first end guard of the first arm 106 and the second end guard of the second arm 108 of the clip 104 are placed furthest apart.

In some embodiments, after the needle 120 has been inserted into the patient's body, the needle 120 may be removed from within the catheter. In order to do this, the clinician may pull the needle 120 towards a proximal end of the catheter adapter 118. In some embodiments, in response to the catch formed on the needle 120 engaging with the second internal diameter of guard bore 116 as described herein, the needle guard 102 may be dragged towards a proximal end of the catheter adapter 118.

In some embodiments, the movement of the needle guard 102 towards the proximal end of the catheter adapter 118 may, initially, cause the stem of the needle guard 102 to pass through the hole 110 while the clip retention feature 112 of the clip 104 is maintained within the catheter adapter 118. In some embodiments, in response to the catch formed on the needle 120 pulling the needle guard 102 further through the catheter adapter 118, the first end guard of the first arm 106 and the second end guard of the second arm 108 may be lifted from off the stepped shoulder portion and may follow up along a core stem formed between the stepped shoulder portion and the center opening. In some embodiments, because this core stem terminates at the center opening, as the needle guard 102 is pulled further towards the proximal end of the catheter adapter 118, the first end guard of the first arm 106 and the second end guard of the second arm 108 may extend into the center opening such that the first end guard and the second end guard intersect with an axis of the guard bore 116 thereby blocking passage of the needle 120 through the guard bore 116 again. In some embodiments, the length of the needle 120 from the terminal end of the needle 120 to the catch formed thereon is shorter than the length of any of the first arm 106 and the second arm 108.

In some embodiments, the operation of the IV device assembly 100 as described herein, therefore, may secure a terminal end of the needle 120 within the needle guard 102. In some embodiments, the needle guard 102 may be fully removed from within the catheter adapter 118 and the terminal end of the needle 120 will remain within the needle guard 102 and prevented from being exposed through the guard bore 116 due to the first end guard of the first arm 106 and second end guard of the second arm 108 preventing passage of the needle 120 out of a distal end of the needle guard 102. Additionally, in some embodiments, the first end guard of the first arm 106 and second end guard of the second arm 108 may be prevented from coming into contact with an exterior surface of the needle 120. Thus, the core stem, the stepped shoulder and the remaining portions of the needle guard 102 and the functions of these elements prevents the needle 120 from being bent or broken by the pressure exerted on it by the first arm 106 and the second arm 108.

Figure 2:
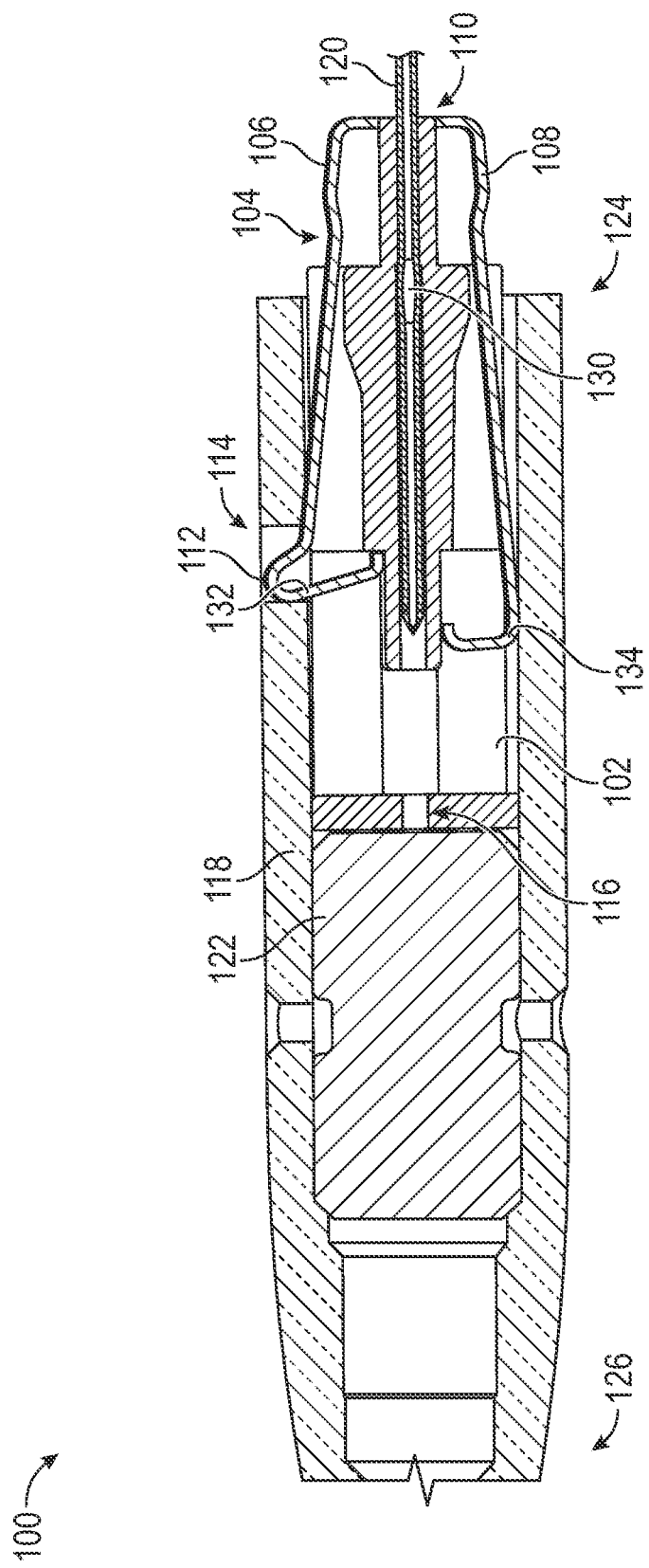
FIG. 2 is a side elevation, section view of an IV device assembly according to an embodiment of the present disclosure.

FIG. 2 is side cross-cut view of an IV device assembly 100 according to some embodiment of the present disclosure. FIG. 2 illustrates the clip 104 in an open configuration, according to some embodiments. That is, the first arm 106 and the second arm 108 of the clip 104 is expanded with the clip retention feature 112 maintained within the window 114 of the catheter adapter 118. In FIG. 2, the needle 120 has been pulled towards the proximal end of the catheter adapter 118, according to some embodiments. The needle 120 has been pulled towards the proximal end 124 of the catheter adapter 118 such that the bump 130 on the needle 120 is in contact with the second internal diameter of the guard bore 116. In some embodiments, at this orientation, the first end guard 132 of the first arm 106 may be resting on the stepped shoulder portion while the second end guard 134 is resting against the core stem surrounding the needle 120.

In some embodiments, at the stage of operation illustrated in FIG. 2, the needle 120 may be pulled back further to cause the needle guard 102 to be pulled away from the septum 122. In some embodiments, in response to this occurring, the clip retention feature 112 of the clip 104 keeps the clip 104 in place while the needle guard 102 moves towards a proximal end of the catheter adapter 118. In some embodiments, the stem formed at the proximal end of the catheter adapter 118 may pass through the hole 110 allowing the needle guard 102 to proceed through the catheter adapter 118. In some embodiments, in response to the needle 120 being pulled further, the second end guard 134 may fall into the center opening formed above the core stem due to a spring bias of the second arm 108 of the clip 104 being directed towards a longitudinal axis of the catheter adapter 118. In some embodiments, in response to the needle 120 being pulled further towards the proximal end of the needle guard 102, the first end guard 132 of the first arm 106 may fall into the center opening formed above the core stem due to a spring bias of the first arm 106 of the clip 104. In some embodiments, as illustrated in FIG. 2, the second end guard 134 may fall into the center opening prior to the first end guard 132 falling into the center opening. This cross-over of the second end guard 134 and the first end guard 132 may place the clip 104 in a second closed configuration. In some embodiments, in this closed configuration, the second end guard 134 and the first end guard 132 are positioned to block motion of the needle 120 towards a distal end of the needle guard 102 and catheter adapter 118.

Figure 3B:
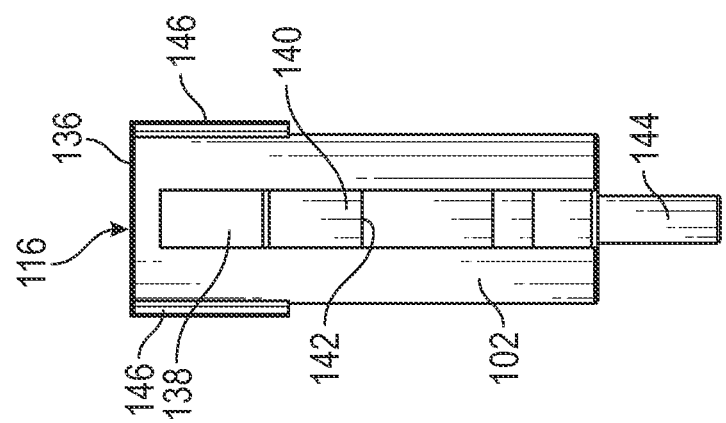
FIG. 3B is a side elevation view of the needle guard according to an embodiment of the present disclosure.
Figure 3A:
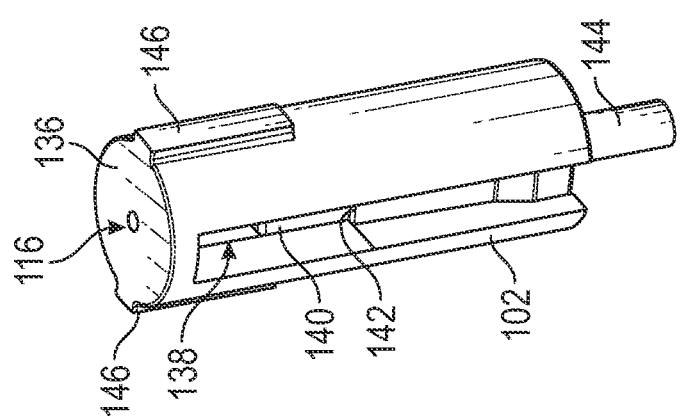
FIG. 3A is a perspective view of a needle guard according to an embodiment of the present disclosure.

FIG. 3A is a perspective view of a needle guard 102, according to some embodiments of the present disclosure. FIG. 3B is a side elevational view of the needle guard 102, according to some embodiments of the present disclosure. FIGS. 3A and 3B illustrate the needle guard 102 without the clip 104 as described in connection with FIGS. 1 and 2. In these views, the stepped shoulder portion 142 is illustrated to be formed intermediary to a proximal end of the needle guard 102 where the stem 144 is formed and a distal end 136 of the needle guard 102, according to some embodiments.

FIGS. 3A and 3B further illustrate that a core stem 140 is formed between the shoulder portion 142 and a center opening 138, according to some embodiments. As described herein, in some embodiments, the shoulder portion 142 and the core stem 140 may cooperate to prevent the first end guard 132 of the first arm 106 and the second end guard 134 of the second arm 108 from coming into contact with a needle (not illustrated in FIGS. 3A and 3B) that is placed within the guard bore 116. Still further, in some embodiments, the core stem 140, the shoulder portion 142, and the remainder of the cut-out through the needle guard 102 form a stepped channel into which the first arm 106 and the second arm 108 may be deformed into when the needle guard 102 is pulled toward a proximal end of the catheter adapter 118.

FIGS. 3A and 3B further illustrate that the needle guard 102 includes multiple rails 146 formed on an exterior surface of the needle guard 102, according to some embodiments. In some embodiments, the rails 146 may mate with a number of channels formed on an interior surface of the catheter adapter 118. In some embodiments, by mating the rails 146 with the channels, the movement of the needle guard 102 may be maintained along a single axis and preventing the needle guard 102 from rotating about the longitudinal axis of the needle guard 102 and the catheter adapter 118.

Figure 3D:
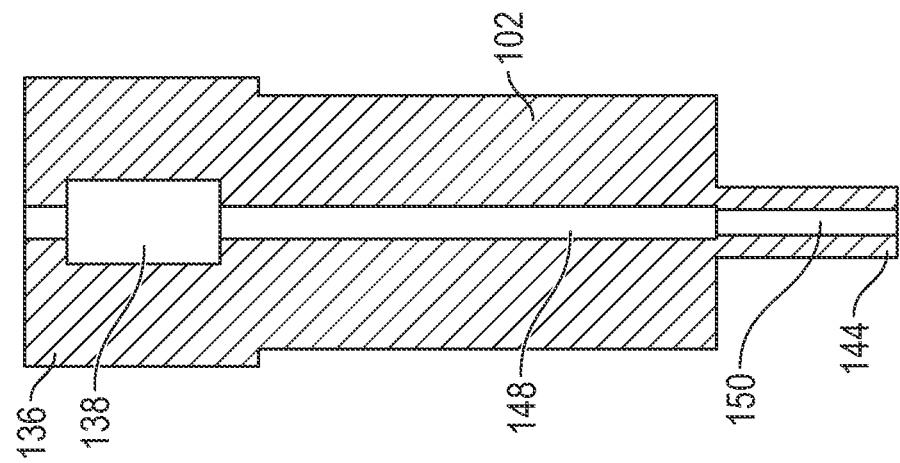
FIG. 3D is a side elevation, section view of the needle guard of FIG. 3C with the needle guard rotated 90 degrees according to an embodiment of the present disclosure.
Figure 3C:
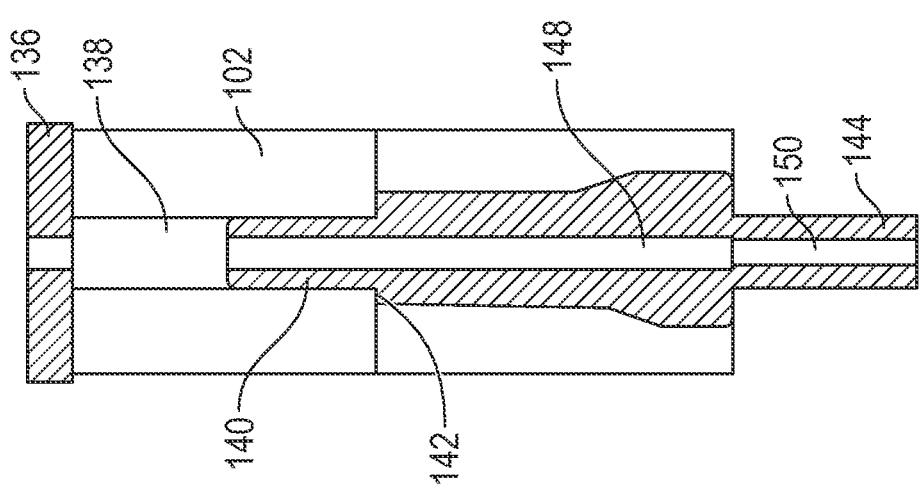
FIG. 3C is a side elevation, section view of the needle guard according to an embodiment of the present disclosure.

FIG. 3C is a side cross-cut view of the needle guard 102, according to some embodiments of the present disclosure. FIG. 3D is a side cross-cut view of the needle guard 102 of FIG. 3C with the needle guard 102 rotated 90 degrees, according to some embodiments of the present disclosure. The cross-cut views illustrate the guard bore 116 having a first internal diameter 148 along a first bore portion of the guard bore 116 and a second internal diameter 150 along a second bore portion of the guard bore 116, according to some embodiments. In some embodiments, the diameter of the second internal diameter 150 may by slightly larger than the smallest diameter of the needle (not illustrated) placed within the guard bore 116. Consequently, a bump 130 formed on the needle may stop the progression of the needle as it is pulled towards a proximal end of the catheter adapter 118 by causing the bump 130 to abut against the interface between the second internal diameter 150 and the first internal diameter 148. In the embodiment illustrated in FIGS. 3C and 3D and other embodiments, the length of the second bore portion having the second internal diameter 150 may be equal to the length of the stem 144 as it extends from a distal end of the needle guard 102.

FIG. 4A is a perspective view of clip 104, according to some embodiments of the present disclosure. FIG. 4B is a side view of a clip 104, according to some embodiments of the present disclosure. Each of the views illustrated in FIGS. 4A and 4B illustrate the clip 104 in a closed configuration as described herein. In some embodiments, the first arm 106 and the second arm 108 may be spring biased towards each other such that separation of the first arm 106 from the second arm 108 creates a force such that the first arm 106 and second arm 108 are elastically drawn together. In some embodiments, when the clip 104 is placed adjacent to the needle guard 102 as illustrated in FIGS. 1 and 2, the spring may bias between the first arm 106 and second arm 108 may be overcome. In some embodiments, it is when the clip 104 is drawn to a proximal end 124 of the catheter adapter 118 as described herein that the first arm 106 and second arm 108 may be brought together again and the first end guard 132 and second end guard 134 come together within the center opening 138.

FIGS. 4A and 4B also illustrate the hole 110 formed through a proximal end of the clip 104, according to some embodiments. Again, in some embodiments, the hole 110 may be formed so as to allow the stem 144 of the needle guard 102 to pass therethrough during use of the IV device assembly 100.

Although FIGS. 4A and 4B illustrate a clip retention feature 112 formed on a single one of the first arm 106 and second arm 108, the present disclosure contemplates that a clip retention feature 112 may be formed on the second arm 108 as well. Again, in some embodiments, the clip retention feature 112 may be placed within a window 114 formed through the catheter adapter 118. In these and other embodiments, a visual inspection of the window 114 by a clinician may indicate to the clinician if and when the catheter adapter 118 is in a closed configuration as described herein or whether the clinician is to pull the needle 120 further in order to pull the needle guard 102 further from within the adapter bore and disengage the clip retention feature 112 from within the window 114. The clinician may, therefore, know whether the needle 120 is secured within the needle guard 102 or not so as to render the catheter adapter 118 safe for disengagement from the IV catheter mechanically coupled to the IV device assembly 100 at the distal end 126 of the IV device assembly 100.

Figure 5:
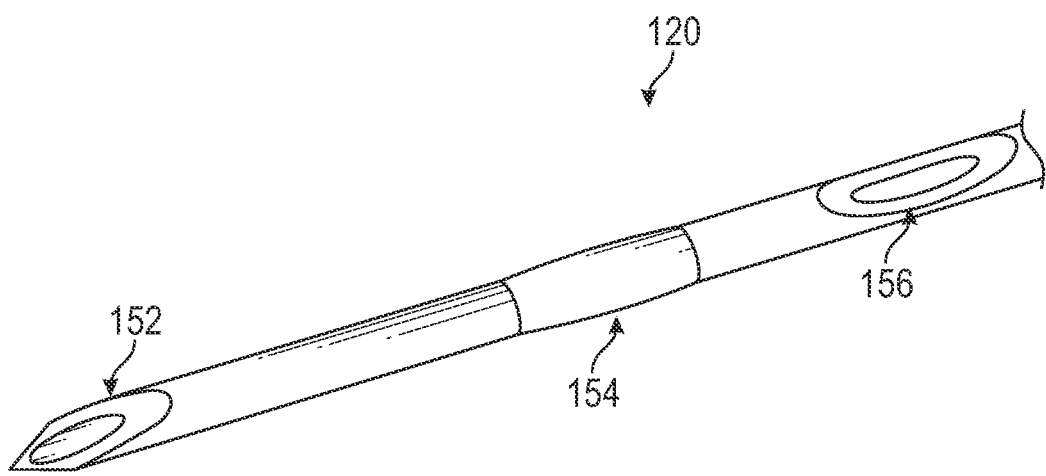
FIG. 5 is a perspective view of a needle according to an embodiment of the present disclosure.

FIG. 5 is a perspective view of a needle 120, according to some embodiments of the present disclosure. FIG. 5 illustrates the bump 154 formed at a location along the needle 120 according to some embodiments. As described herein, in some embodiments, the bump 154 may interface with a second internal diameter 150 of the guard bore 116 to allow for the selective pulling of the needle guard 102 from within the adapter bore in the catheter adapter 118.

In some embodiments, the needle 120 may also include a bevel end 152. As described herein, in some embodiments, the bevel end 152 may be used to insert the needle 120 into a patient's body. In some embodiments, after the needle 120 has been used for this purpose, the bevel end 152 may be dangerous if not encased by the needle guard 102.

The needle 120 may also, in some embodiments, include a detent 156. In some embodiments, the detent 156 may be a notch formed into the needle 120 that may be matted up with a bump formed in the second bore portion of the guard bore 116. In these and other embodiments, the bump 154 and the detent 156 may be used to prevent movement of the needle 120 relative to the needle guard 102 after the bevel end 152 of the needle 120 has passed into the core stem 140 as described herein.

Figure 6C:
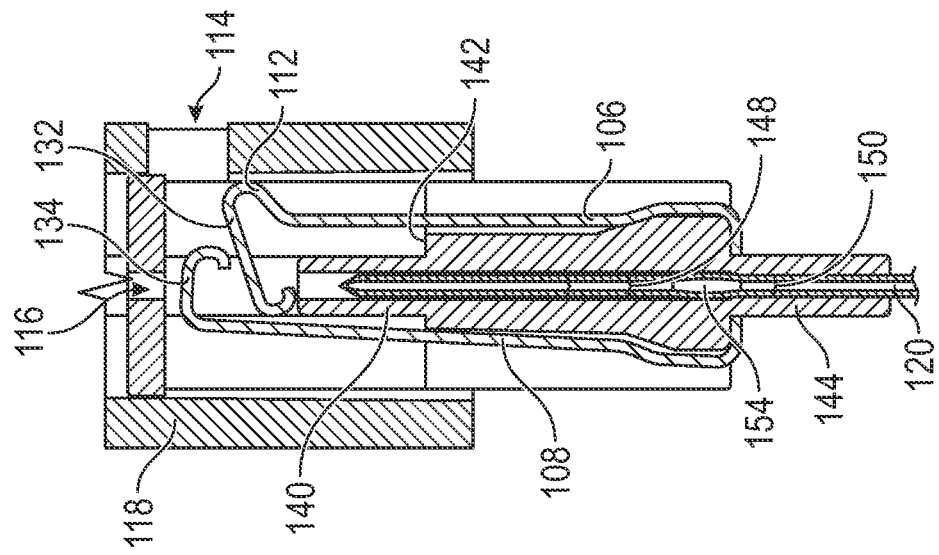
FIG. 6C is a side elevation, section view of an IV device assembly according to an embodiment of the present disclosure.
Figure 6D:
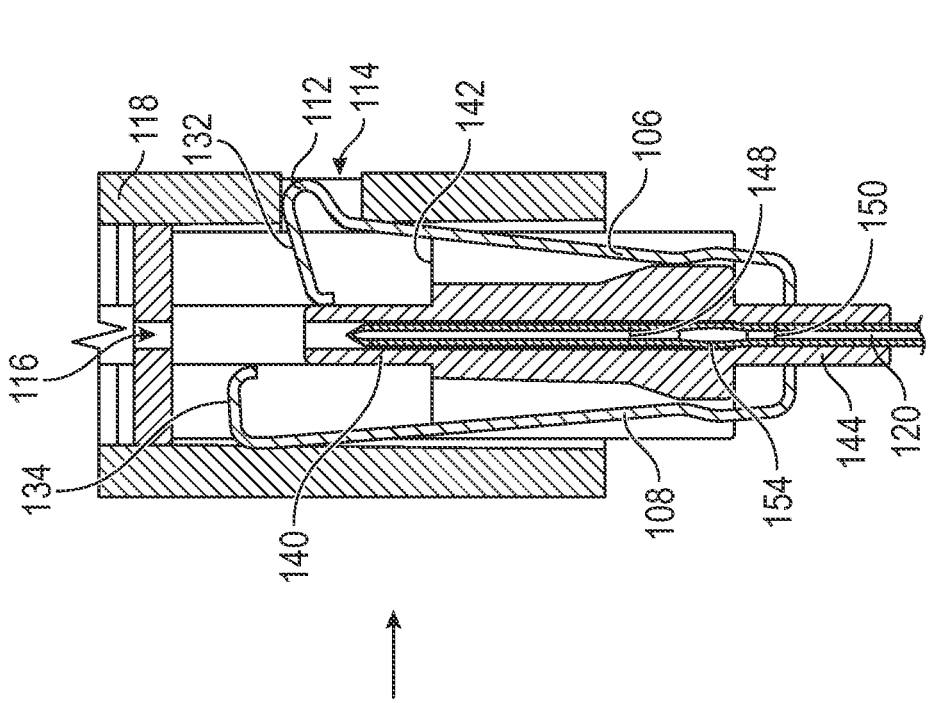
FIG. 6D is a side elevation, section view of an IV device assembly according to an embodiment of the present disclosure.

FIG. 6A is a cross-cut side view of an IV device assembly, according to some embodiments of the present disclosure. FIG. 6B is a cross-cut side view of an IV device assembly, according to some embodiments of the present disclosure. FIG. 6C is a cross-cut side view of an IV device assembly, according to some embodiments of the present disclosure. FIG. 6D is a cross-cut side view of an IV device assembly, according to some embodiments of the present disclosure. FIGS. 6A through 6D illustrate different stages of progression of the IV device assembly 100 as the needle 120 and the needle guard 102 are advanced to a proximal end of the catheter adapter 118, according to some embodiments. As described herein, in some embodiments, operation of the IV device assembly 100 secures a bevel end 152 of the needle 120 within the needle guard 102. In order to initiate this process, in some embodiments, a clinician or other HCP may pull the needle 120 towards a proximal end of the catheter adapter 118. FIG. 6A illustrates that the bevel end 152 of the needle 120 has been pulled into the needle guard 102 and just past a distal end of the needle guard 102, according to some embodiments. In some embodiments, at this stage in the operation of the IV device assembly 100, the bump 154 has not interfaced with the second internal diameter 150 of the guard bore 116 and, therefore, the needle guard 102 has not moved in a proximal direction relative to the catheter adapter 118.

FIG. 6B does illustrate that the bump 154 on the needle 120 has interfaced with the second internal diameter 150, according to some embodiments. In FIG. 6B, the bevel end 152 of the needle 120 has passed below a terminal end of the core stem 140, according to some embodiments. The first end guard 132 of the first arm 106 has not been moved relative to the stepped shoulder portion 142 and the second end guard 134 of the second arm 108 has not moved from its original position against the core stem 140, according to some embodiments. Still further, the clip retention feature 112 is maintained within the window 114 formed through the catheter adapter 118, according to some embodiments.

FIG. 6C illustrates that as the needle 120 has been pulled further by the clinician, the needle guard 102 has moved proximally relative to the clip 104 which has remained in place with its clip retention feature 112 within the window 114, according to some embodiments. Additionally, the stem 144 has progress through the hole 110 so as to allow the needle guard 102 to move relative to the clip 104 that, for this figure, remains stationary.

FIG. 6D illustrates the IV device assembly 100 with the clip 104 in a closed configuration, according to some embodiments. In this figure, the needle 120 has been pulled sufficiently so that the needle guard 102 has mechanically engaged with the clip 104 such that the movement of the needle guard 102 also drags the clip 104 with it towards a proximal end of the catheter adapter 118, according to some embodiments. In the closed configuration, the clip retention feature 112 has been disengaged from within the window 114 and the first arm 106 and second arm 108 have been allowed to pass into the center opening 138, according to some embodiments. Again, the spring bias of the first arm 106 and second arm 108 causes the first end guard 132 of the first arm 106 and the second end guard 134 of the second arm 108 drag against the surfaces of the stepped channel without coming into contact with an exterior surface of the needle 120. In this fashion, the needle 120 may be secured within the needle guard 102 such that movement of the needle 120 distally can not occur.

Figure 7:
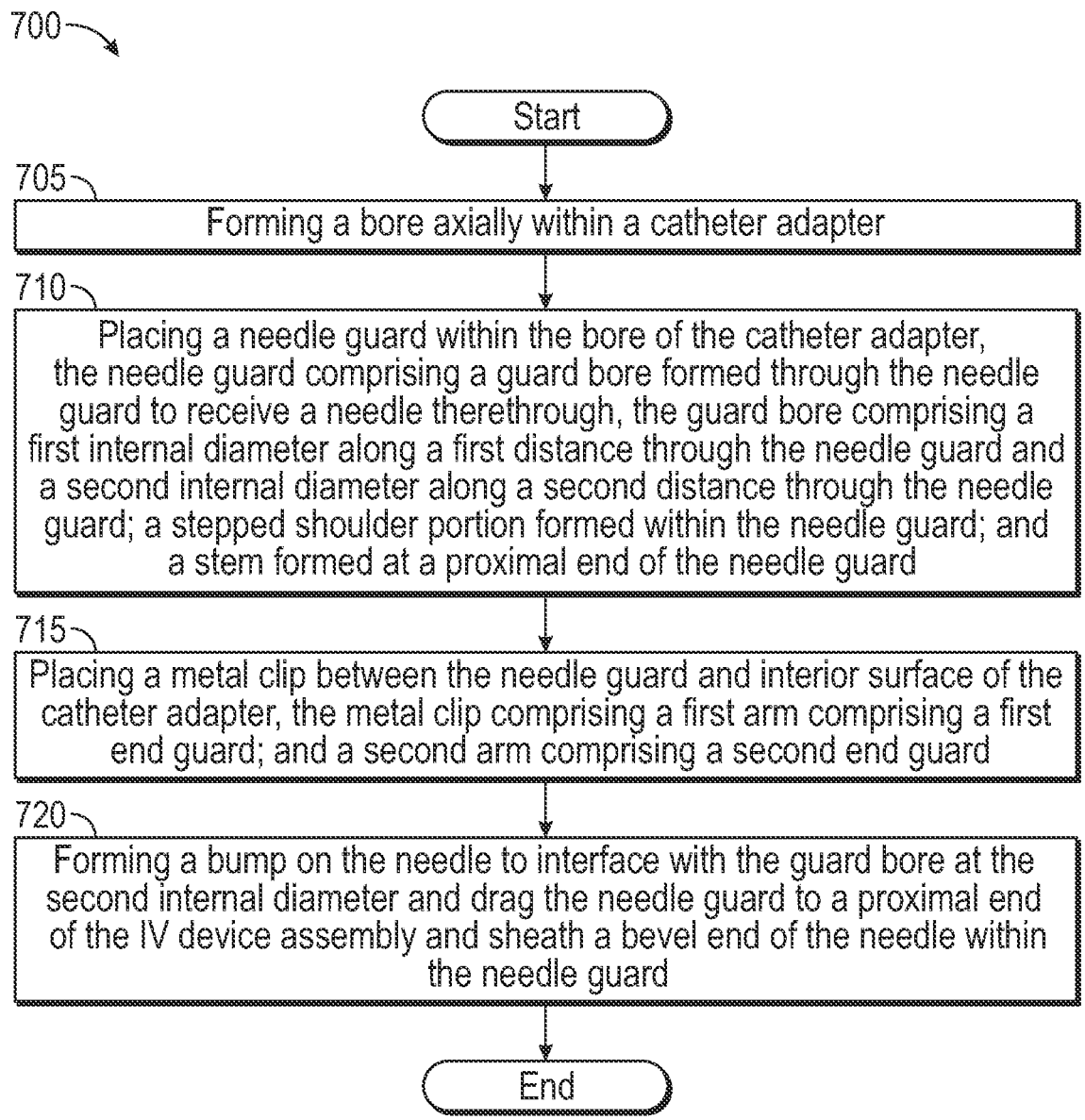
FIG. 7 is a flowchart illustrating a method of manufacturing an IV device assembly according to an embodiment of the present disclosure.

FIG. 7 is a flowchart illustrating a method 700 of manufacturing an IV device assembly, according to some embodiments of the present disclosure. In some embodiments, the method 700 may include forming a bore axially within a catheter adapter at block 705. In some embodiments, the formation of the bore may be completed using any type of additive or subtractive manufacturing process.

The method 700 may include, at block 710, placing a needle guard within the bore of the catheter adapter. In some embodiments, the needle guard may include a guard bore formed through the needle guard to receive a needle therethrough. In some embodiments, the guard bore may include a first internal diameter along a first distance through the needle guard and a second internal diameter along a second distance through the needle guard; a stepped shoulder portion formed within the needle guard; and a stem formed at a proximal end of the needle guard.

The method 700 may also include, at block 715, placing a metal clip between the needle guard and interior surface of the catheter adapter. In some embodiments, the metal clip may include a first arm, which may include a first end guard, and a second arm, which may include a second end guard. The method 700 may also include, at block 720, forming a bump on the needle to interface with the guard bore at the second internal diameter and drag the needle guard to a proximal end of the IV device assembly and sheath a bevel end of the needle within the needle guard.

The IV device assembly described herein may prevent the clip from coming into contact with the needle. This prevents damage to the needle as well as damage to the body of a patient during withdrawal of the needle from within the catheter adapter of the IV device assembly. In some embodiments, because the clip is made of a metal and because the needle guard is made of a plastic, the friction created between these two forces may be reduced thereby allowing for less force to be applied to the needle when withdrawing the needle guard from within the catheter adapter.

All examples and conditional language recited herein are intended for pedagogical objects to aid the reader in understanding the invention and the concepts contributed by the inventor to furthering the art, and are to be construed as being without limitation to such specifically recited examples and conditions. Although embodiments of the present disclosure have been described in detail, it should be understood that the various changes, substitutions, and alterations could be made hereto without departing from the spirit and scope of the disclosed embodiments.

The invention claimed is:

1. An intravenous (IV) device assembly, comprising:
a catheter adapter comprising a distal end, a proximal end, and an adapter bore formed axially therein;
a needle;
a needle guard residing within the adapter bore of the catheter adapter, the needle guard comprising:
a guard bore formed through the needle guard to receive the needle therethrough, the guard bore comprising:
a first internal diameter along a first bore portion of the guard bore;
a second internal diameter, smaller than the first internal diameter along the first bore portion, along a second bore portion of the guard bore; and
a stepped shoulder portion disposed distal to the second internal diameter, wherein the stepped shoulder portion comprises a surface generally perpendicular to a longitudinal axis of the IV device assembly; and
an exterior surface; and
a clip coupled to the exterior surface, the clip comprising:
a clip retention feature that cooperates with a catheter adapter retention feature of the catheter adapter to urge the needle guard to remain in place within the adapter bore;
a first arm comprising a first end guard; and
a second arm comprising a second end guard; wherein:
the second internal diameter is sufficiently small to urge the needle to remain within the needle guard; and
the clip is slidable distally along the exterior surface, wherein in response to a proximal withdrawal of the needle, the clip slides from an open configuration, in which the needle is movable distally within the needle guard, to a closed configuration, wherein in the closed configuration at least one of the first end guard and the second end guard is positioned to block distal motion of the needle within the needle guard,
wherein the needle guard comprises an elongated slot, wherein the first arm extends through the elongated slot when the clip is in the open configuration, wherein when the clip is in the open configuration, a proximal end of the clip is proximal to the elongated slot and spaced apart from a proximal end of the needle guard, wherein in response to the proximal withdrawal of the needle and movement of the clip from the open configuration to the closed configuration, the proximal end of the needle guard contacts the proximal end of the clip and the elongated slot moves proximally with respect to the clip such that a proximal end of the elongated slot is generally aligned with the proximal end of the clip,
wherein the stepped shoulder portion prevents the first end guard and the second end guard from contacting the needle, wherein in the open configuration, the first end guard is configured to contact the surface of the stepped shoulder portion when the second end guard contacts the needle guard distal to the surface of the stepped shoulder portion.

2. The IV device assembly of claim 1, further comprising a hole formed in the clip through which a stem of the needle guard is selectively passed as the needle guard and the clip pass through the catheter adapter.

3. The IV device assembly of claim 1, further comprising a septum placed between the needle guard and the distal end of the catheter adapter for the needle to pierce and exit a distal end of the IV device assembly.

4. The IV device assembly of claim 1, further comprising a bump formed on the needle to interface with the guard bore at the second internal diameter and drag the needle guard to a proximal end of the IV device assembly and sheath a bevel end of the needle within the needle guard in response to the proximal withdrawal of the needle guard from the adapter bore.

5. The IV device assembly of claim 1, further comprising a plurality of rails formed on the needle guard to interface with an interior surface of the catheter adapter to restrict rotation of the needle guard from the adapter bore in response to the withdrawal of the needle guard from the adapter bore.

6. The IV device assembly of claim 1, further comprising a stepped channel formed within the needle guard to allow the first arm and the second arm to be deformed into the needle guard.

\* \* \* \* \*